US00PP18988P2

(12) United States Plant Patent
Kormann

(10) Patent No.: US PP18,988 P2
(45) Date of Patent: Jun. 24, 2008

(54) ***LOBELIA* PLANT NAMED 'BALWALILA'**

(50) Latin Name: *Lobelia erinus*
Varietal Denomination: Balwalila

(76) Inventor: Luise Kormann, Hessenweg 6, 48703 Stadtlohn (DE)

( * ) Notice: Subject to any disclaimer, the term of this patent is extended or adjusted under 35 U.S.C. 154(b) by 0 days.

(21) Appl. No.: 11/725,370

(22) Filed: Mar. 19, 2007

(51) Int. Cl.
*A01H 5/00* (2006.01)

(52) U.S. Cl. ..... Plt./451

(58) Field of Classification Search ..... Plt./451
See application file for complete search history.

*Primary Examiner*—Kent L. Bell
*Assistant Examiner*—S. B. McCormick/Ewoldt
(74) *Attorney, Agent, or Firm*—Audrey Charles

(57) ABSTRACT

A new and distinct cultivar of *Lobelia* plant named 'Balwalila', characterized by its violet-colored flowers, dark green-colored foliage; and vigorous, compact-mounded, semi-trailing growth habit.

1 Drawing Sheet

Latin name of genus and species of plant claimed: *Lobelia erinus*.
Variety denomination: 'Balwalila'.

BACKGROUND OF THE INVENTION

The present invention relates to a new and distinct cultivar of *Lobelia* plant botanically known as *Lobelia erinus* and hereinafter referred to by the cultivar name 'Balwalila'.

The new cultivar originated in a controlled breeding program in Südlohn, Germany during the summer of 2002. The objective of the breeding program was the development of *Lobelia* cultivars with unique flower coloration and a vigorous, mounded, and semi-trailing growth habit.

The new *Lobelia* cultivar is the result of cross-pollination. The female (seed) parent of the new cultivar is the proprietary *Lobelia erinus* breeding selection designated 02P616, not patented, characterized by its pink-colored flowers, small, fine dark green-colored foliage, and loose, moderately vigorous growth habit. The male (pollen) parent of the new cultivar is the proprietary *Lobelia erinus* breeding selection designated 02P508, not patented, characterized by its large intensely blue-colored flowers, dark green-colored foliage, and upright growth habit. The new cultivar was discovered and selected as a single flowering plant within the progeny of the above stated cross-pollination during the spring of 2003 in a controlled environment at Südlohn, Germany.

Asexual reproduction of the new cultivar by terminal stem cuttings since late summer 2003 at Südlohn, Germany has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balwalila' as a new and distinct cultivar of *Lobelia* plant:

1. Violet-colored flowers;
2. Dark green-colored foliage; and
3. Vigorous, compact-mounded, semi-trailing growth habit.

Plants of the new cultivar differ from plants of the female parent primarily in flower color, foliage size, and growth habit and from plants of the male parent primarily in flower size, flower color, leaf size, and growth habit.

Of the many commercially available *Lobelia* cultivars known to the inventor, the most similar in comparison to the new cultivar is 'Wespinstar', U.S. Plant Pat. No. 17,963. However, in side by side comparison conducted in Südlohn, Germany, plants of the new cultivar differ from plants of 'Wespinstar' in the following characteristics:

1. Plants of the new cultivar have smaller leaves than plants of 'Wespinstar'.
2. Plants of the new cultivar have shorter pedicles than plants of 'Wespinstar'; and
3. Plants of the new cultivar have a flower color different from plants of 'Wespinstar'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balwalila'. The plants were grown in 12 cm pots for 27 weeks in a greenhouse at S üdlohn, Germany.

DETAILED BOTANICAL DESCRIPTION

Figure 1:
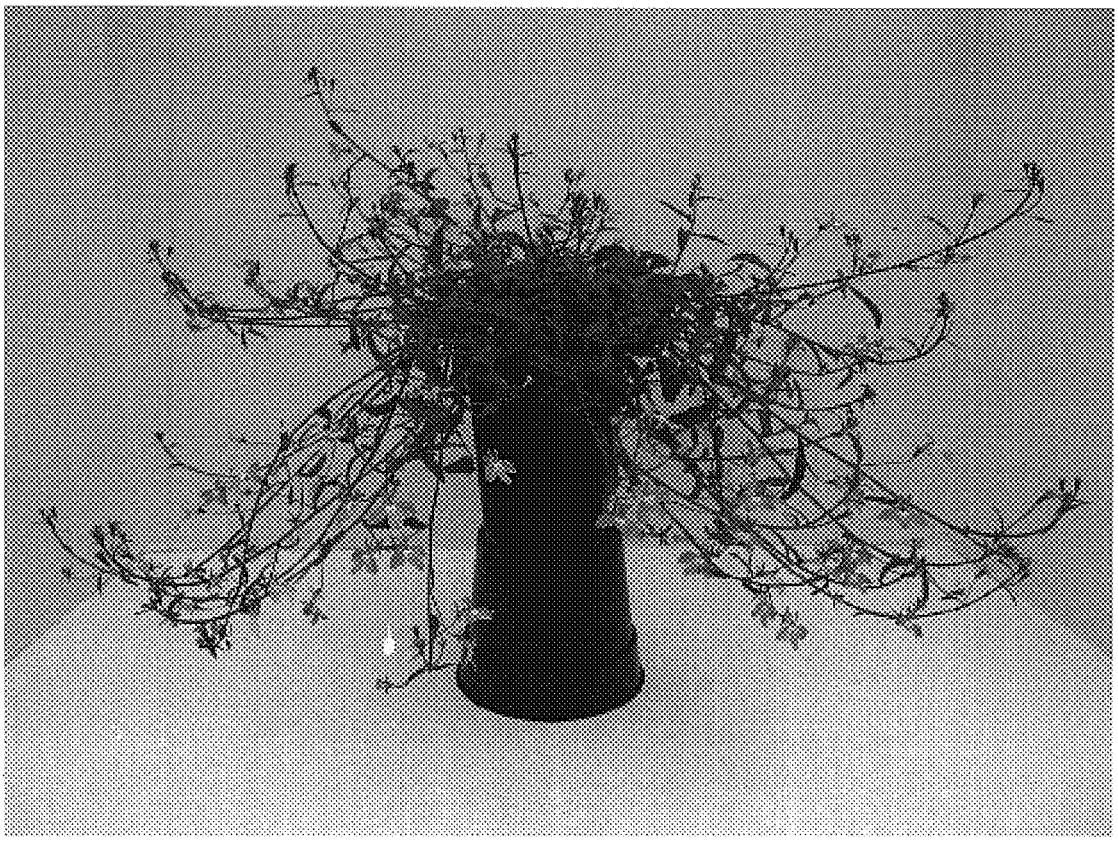
FIG. 1 illustrates a side view of the overall growth and flowering habit of 'Balwalila'.
Figure 2:
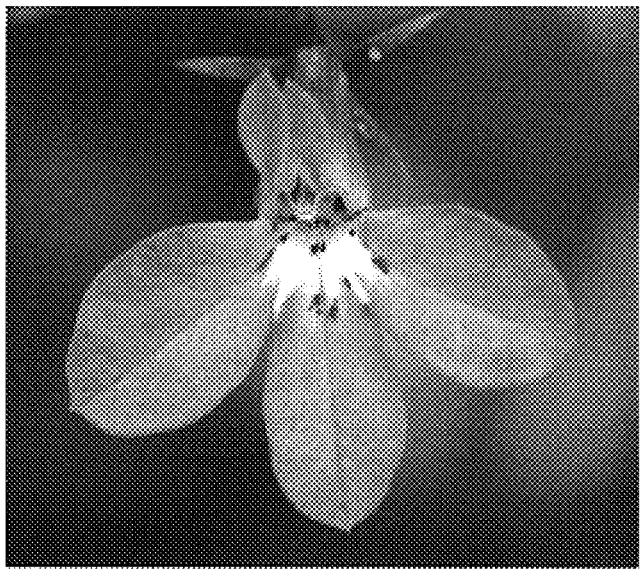
FIG. 2 illustrates a close-up view of an individual flower of 'Balwalila'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined during the week of Aug. 28, 2006 under natural light conditions is Südlohn, Germany.

The following descriptions and measurements describe plants produced from cuttings taken from stock plants and grown in a glass-covered greenhouse under conditions comparable to those used in commercial practice. The plants were grown one plant per 12 cm pot or three plants per 25 cm hanging basket for 27 weeks utilizing a soilless growth medium. Greenhouse temperatures were maintained at approximately 68° F. to 77° F. (20° C. to 25° C.) during the day and approximately 61° F. to 65° F. (16° C. to 18° C.) during the night. Greenhouse light levels of 3,000 lux to 50,000 lux were maintained during the day. Plants were pinched twice during the production period by removing about 1 to 2 cm of the uppermost apical growing tip.

Botanical classification: *Lobelia erinus* cultivar Balwalila.

Parentage:

*Female parent.*—Proprietary *Lobelia erinus* breeding selection designated 02P616, not patented.

*Male parent.*—Proprietary *Lobelia erinus* breeding selection designated 02P508, not patented.

Propagation:

*Type cutting.*—Terminal stem.

*Time to initiate roots.*—Approximately 10 to 14 days.

*Time to produce a rooted cutting.*—Approximately 24 to 28 days, with approximately 3 to 4 additional days during winter months.

*Root description.*—Fine, fibrous.

*Rooting habit.*—Freely branching.

Plant description:

*Commercial crop time.*—Approximately 16 to 20 weeks to produce a 12 cm basket from a rooted cutting.

*Growth habit and general appearance.*—Vigorous, compact-mounded, semi-trailing.

*Size.*—Height from soil level to top of plant plane: Approximately 15 to 18 cm. Width: Approximately 39 cm.

*Branching habit.*—Freely basal branching, pinching improves habit. Quantity of lateral branches per plant: Approximately one per node.

*Branch.*—Shape: Square. Strength: Strong, flexible. Length: Approximately 18.5 cm. Diameter: Approximately 2.7 mm. Length of central internode: Approximately 1.2 cm. Texture: Glabrous. Color of young and mature stems: 147A.

Foliage description:

*General description.*—Form: Simple. Arrangement: Alternate. Venation pattern: Pinnate. Texture of upper surface: Glabrous, satiny. Texture of lower surface: Glabrous, dull. Color of upper surface of young foliage: 137A with venation of 137B. Color of lower surface of young foliage: 137C with venation of 137D. Color of upper surface of mature foliage: 147A with venation of 147B. Color of lower surface of mature foliage: Between 147B and 147C with venation of between 147C and 147D.

*Lower leaves.*—Aspect: Acute angle to stem. Shape: Oblanceolate. Margin: Crenate. Apex: Obtuse. Base: Attenuate. Length of mature leaf: Approximately 4.0 cm. Width of mature leaf: Approximately 2.5 cm.

*Mid-plant leaves.*—Aspect: Acute angle to stem. Shape: Elliptic. Margin: Crenate. Apex: Acute. Base: Attenuate. Length of mature leaf: Approximately 2.5 cm. Width of mature leaf: Approximately 1.5 cm.

*Upper leaves.*—Aspect: Obtuse angle to stem. Shape: Linear. Margin: Entire. Apex: Acute. Base: Sessile. Length of mature leaf: Approximately 1.9 cm. Width of mature leaf: Approximately 4.0 mm.

Flowering description:

*Flowering habit.*—'Balwalila' is freely flowering under outdoor growing conditions with substantially continuous blooming from spring through autumn and year-round in greenhouse environment. Flowers are persistent. Older flowers are overgrown by new flower and foliage.

*Flowering response time.*—Approximately 10 to 12 weeks.

Inflorescence description:

*General description.*—Type: Loose raceme. Fragrance: None. Length or height: Approximately 12.5 cm. Width: Approximately 4 to 5 cm. Quantity of fully open flowers per inflorescence: Approximately 8 to 10. Quantity of fully open flowers per lateral stem: Approximately 10 to 15.

*Peduncle.*—Strength: Strong, flexible. Length: Approximately 11.5 cm. Diameter: Approximately 1.0 mm. Texture: Glaborous. Color: 147A.

Flower description:

*Type.*—Solitary at lateral apices, zygomorphic, bilabiate. Flowers are resupinate because of a half twist in the pedicel. Aspect: Outward facing.

*Bud.*—Rate of opening: Generally takes 1 to 2 days for bud to progress from first color to fully open flower. Quantity per lateral stem: Approximately 6.

*Bud just before opening.*—Shape: Oblong. Length: Approximately 8.6 mm. Diameter: Approximately 2.9 mm. Color: 193B combined with 182D at tip, 193B in center, and 145D at base.

*Corolla.*—Shape: Bilabiate having an upper lip of two narrow petals and a lower lip of three petals. Petals are fused at the base forming a tube that is split between the two upper petals. Length: Approximately 1.5 cm. Diameter: Approximately 1.8 cm.

*Petals.*—Upper petals: Quantity: 2. Shape: Spatulate. Margin: Entire. Apex: Cuspidate. Length from throat: Approximately 5.2 mm. Width: Approximately 1.9 mm. Lower petals: Quantity: 3. Shape: Oblong. Margin: Entire. Apex: Mucronate. Length from throat: Approximately 1.2 cm. Width: Approximately 5.6 mm. Texture of upper surface: Glabrous, satiny. Texture of lower surface: Glabrous, dull. Color of upper surface when first open: N80A. Color of lower surface when first open: 76D. Color of upper surface when fully open: N80B with age fading to N80A. Color of lower surface when fully open: 76C with age fading to 76B. Throat: 155C with two streaks of 144A and spots of N81A.

*Corolla tube.*—Length: Approximately 6.9 mm. Diameter at base: Approximately 2.3 mm. Diameter at throat: Approximately 3.5 mm. Color: 76D with two stripes of 144B.

*Sepals.*—Arrangement: Single whorl, star-shaped calyx. Quantity per flower: 5, fused at base. Shape: Linear. Apex: Acute. Length: Approximately 4.0 mm. Width: Approximately 1.3 mm. Texture of upper and lower surfaces: Pubescent. Color of upper and lower surfaces: 147A.

*Pedicel.*—Strength: Wiry, flexible. Aspect: Acute angle to stem. Length: Approximately 1.4 cm. Diameter: Approximately less than 1.0 mm. Texture: Glabrous. Color: 147A.

*Reproductive organs.*—Androecium: Stamen quantity: 5 per flower, anthers and upper half of filaments connate. Filament length: approximately 4.5 mm. Filament color: Ranges from 84A through 84D. Anther shape: Linear. Anther length: Approximately 2.1 mm. Anther width: Approximately 1.1 mm. Anther color: N187A. Pollen amount: Moderate. Pollen color: 9A. Gynoecium: Pistil quantity: 1 per flower. Pistil length: Approximately 8.5 mm. Stigma shape: Bilobed, ovoid. Stigma color: N77A with white pubescence transitioning as matures to 176B. Style length: Approximately 5.0 mm. Style color: 144B. Ovary color: Between 137A and 137B.

Seed and fruit production: Neither seed not fruit production has been observed.

Disease and pest resistance: Resistance to pathogens and pests common to *Lobelia* has not been observed.

Temperature tolerance: Plants of the *Lobelia* have been observed to tolerate low temperatures of 5 to 8° C. and to be moderately resistant to high temperatures.

What is claimed is:

1. A new and distinct cultivar of *Lobelia* plant named 'Balwalila', substantially as herein shown and described.

* * * * *